US012577613B2

(12) United States Patent
Rogerson et al.

(10) Patent No.: US 12,577,613 B2
(45) Date of Patent: Mar. 17, 2026

(54) SYSTEMS AND METHODS FOR SELECTIVE DNA MULTIPLE DISPLACEMENT AMPLIFICATION OF A DNA MIXTURE

(71) Applicant: Genomic Labs Ltd

(72) Inventors: Daniel Rogerson, Bristol (GB); Joshua Dyer, Bristol (GB)

(73) Assignee: Genomic Labs Ltd, Bristol (GB)

( * ) Notice: Subject to any disclaimer, the term of this patent is extended or adjusted under 35 U.S.C. 154(b) by 0 days.

(21) Appl. No.: 19/091,172

(22) Filed: Mar. 26, 2025

(65) Prior Publication Data

US 2025/0283160 A1 Sep. 11, 2025

Related U.S. Application Data

(63) Continuation of application No. PCT/GB2023/052501, filed on Sep. 27, 2023.

(30) Foreign Application Priority Data

Sep. 27, 2022 (GB) ..................................... 2214125

(51) Int. Cl.
| | |
|---|---|
| *C12P 19/34* | (2006.01) |
| *C12Q 1/34* | (2006.01) |
| *C12Q 1/48* | (2006.01) |
| *C12Q 1/6848* | (2018.01) |
| *C12Q 1/686* | (2018.01) |

(52) U.S. Cl.
CPC ............. *C12Q 1/6848* (2013.01); *C12Q 1/34* (2013.01); *C12Q 1/485* (2013.01); *C12Q 1/686* (2013.01); *G01N 2333/9126* (2013.01); *G01N 2333/922* (2013.01)

(58) Field of Classification Search
CPC ................................................... C12Q 1/6844
See application file for complete search history.

(56) References Cited

U.S. PATENT DOCUMENTS

| | | |
|---|---|---|
| 2015/0315636 A1 | 11/2015 | Nadeau et al. |
| 2019/0085318 A1 | 3/2019 | Shuber |
| 2019/0203280 A1 | 7/2019 | Shin et al. |
| 2021/0040537 A1 | 2/2021 | Shuber |
| 2023/0031001 A1* | 2/2023 | Fujita ...................... C12N 9/12 |

FOREIGN PATENT DOCUMENTS

| | | |
|---|---|---|
| EP | 4047091 A1 | 8/2022 |
| WO | 2019079656 A1 | 4/2019 |

| | | |
|---|---|---|
| WO | 2020006036 A1 | 1/2020 |
| WO | 2020119721 | 6/2020 |
| WO | 2021075555 A1 | 4/2021 |

OTHER PUBLICATIONS

EP Search Report in GB2214125.3 dated Mar. 16, 2023.
Hiroshi Nishimasu et al., "Crystal Structure of *Staphylococcus aureus* Cas9". Cell. Aug. 27, 2015; 162(5):1113-26. doi: 10.1016/j.cell.2015.08.007. PMID: 26317473; PMCID: PMC4670267.
International Search Report in PCT/GB2023/052501 dated Dec. 22, 2023.
Qian Zhang et al., "The post-PAM interaction of RNA-guided spCas9 with DNA dictates its target binding and dissociation," Science Advances, vol. 5, No. 11, Nov. 1, 2019 (Nov. 1, 2019), XP093110997, us ISSN: 2375-2548.
Siqi Zhang et al., "Dynamics of *Staphylococcus aureus* Cas9 in DNA target Association and Dissociation," EMBO Reports, Nature Publishing Group, London, GB, vol. 21, No. 10, Aug. 13, 2020 (Aug. 13, 2020), page n/a, XP072243407, ISSN: 1469-221X.
Wenhua Zhou et al., "A CRISPR-Cas9-triggered strand displacement amplification method for ultrasensitive DNA detection," Nature Communications, vol. 9, No. 1, Nov. 27, 2018 (Nov. 27, 2018), XP055611060.
International Preliminary Report on Patentability (IPRP) in PCT/GB2023/052501 dated Dec. 11, 2024.
Written Opinion in PCT/GB2023/052501 dated Dec. 22, 2023.

* cited by examiner

*Primary Examiner* — Kenneth R Horlick
(74) *Attorney, Agent, or Firm* — Veros Legal Solutions, LLP

(57) ABSTRACT

A method of selective DNA amplification of a DNA mixture comprising a first population of DNA and a second population of DNA, wherein:— a) a catalytically dead *Staphylococcus aureus* Cas9 complex (dSaCas9) comprising a dSaCas9 protein or derivative thereof complexed with one or more guide RNAs having selective binding affinity for DNA sequences preferentially present in the first population of DNA compared to the second population of DNA is contacted with the DNA mixture under a first reaction condition, said first reaction condition being suitable for binding of the dSaCas9 complex to DNA sequences for which it has a binding affinity, and then b) a strand-displacing DNA polymerase is contacted with the DNA mixture under a second reaction condition, said second reaction condition being suitable for amplification being suitable for amplification activity of the strand-displacing DNA polymerase; and related kits and uses.

18 Claims, 4 Drawing Sheets

Specification includes a Sequence Listing.

SYSTEMS AND METHODS FOR SELECTIVE DNA MULTIPLE DISPLACEMENT AMPLIFICATION OF A DNA MIXTURE

CROSS-REFERENCE TO RELATED APPLICATIONS

This application is a Continuation of PCT Application No. PCT/GB2024/052501, filed Sep. 27, 2023, which claims the benefit of GB Application No. 2214125.3, filed on Sep. 22, 2022, the entire contents of each are hereby incorporated by reference in their entirety.

FIELD OF INVENTION

The invention relates to improvements in nucleic acid amplification methods. More specifically it relates to methods of improving the specificity of nucleic acid amplification methods by selectively suppressing amplification of non-target sequences. Also encompassed by the invention are related products and uses.

BACKGROUND

Identifying specific DNA from complex samples containing a diversity of DNA sequences from a range of sources is a technical challenge, which is sometimes solved by use of the polymerase chain reaction (PCR) or equivalent nucleic acid amplification methods (including isothermal amplification cycling and strand-displacement methods). PCR uses sequence-specific primers for a target sequence and typically amplifies a short sequence between primers using a polymerase such as Taq polymerase. Amplification of non-target sequences may be suppressed by use of a blocking oligonucleotide primer such as described in US2015/0315636 and WO2020/119721. A blocking primer hybridises between the two amplification primers and prevents chain extensions (for example, by use of chemical modification pf the blocking primer which resists strand extension), and thereby amplification of the non-target sequences.

A major drawback of conventional PCR and certain other methods of targeted amplification is that whilst they are useful for amplification of specific target sequences of which you have prior knowledge, there are some applications where the user does not fully know what sequence he or she is looking for until it has been found. Fortunately, whole genome sequencing has become inexpensive and readily available. It has great potential to contribute to overcoming this problem. An example of an application for which whole genome sequencing has the potential to become useful is the detection of very low levels of unknown pathogenic organisms (e.g., bacteria, fungi and viruses) in the blood from human patients with suspected sepsis. By sequencing all pathogenic nucleic acids (or a relatively large proportion thereof) in a sample (for example a blood sample) taken from a human subject, the detection and characterisation of all pathogen species present can be carried out. Detection of pathogen in blood may be especially challenging if the pathogen is present at very low level because target DNA copy number will also be very low. Detection of pathogens at low levels is especially useful if a disease such as sepsis is to be detected sufficiently-early so that the chances of patient survival and recovery are increased. Prior to whole genome sequencing, target DNA copy number may be increased in a non-sequence-specific fashion by enzymatic amplification using random (for example, random hexamer) primers. PCR amplification using an enzyme such as Taq polymerase is suitable for amplification of short runs of nucleic acid. It is not suitable for amplification of long stretches of nucleic acid prior to whole genome sequencing, one reason being that it lacks proof reading ability. Suitable amplification techniques for long run amplifications typically use highly progressive strand displacement nucleic acid polymerases such as phi (Φ) DNA polymerase which can produce very large DNA amplification with a low error rate in a process known as multiple displacement amplification (MDA). MDA generates large product sizes with low error. It works at a constant temperature and uses non-sequence specific primers (typically random hexamers with 3' modification to resist the 3' to 5' exonuclease activity of Φ29DNA polymerase). MDA uses a strand displacement polymerase. This means that as the newly synthesised strand extends, the polymerase encounters other amplification products (primers extended by other polymerase molecules). Those amplification products are displaced by the strand displacement DNA polymerase resulting in single-stranded displaced DNA which is able to serve as a template for further primer annealing. Thus a strand displacing DNA polymerase is able to amplify rapidly large target sequences with a low error rate. The products of strand displacement polymerisation are thus especially suitable for use in whole genome sequencing for example next generation sequencing (NGS).

There are challenges to amplifying pathogen DNA (for example bacterial DNA for whole genome sequencing) from samples obtained from human subjects because such samples tend to be "swamped" by human DNA. This issue is especially pertinent when multiple displacement amplification is used because there is no amplification selectivity. There is therefore a need to differentially amplify pathogen DNA (for example bacterial DNA) in preference to human DNA and/or to selectively inhibit the amplification of human DNA versus pathogen DNA (for example bacterial DNA). Such a method should preferably be an MDA method if the resultant pathogen DNA (for example bacterial DNA) is to be suitable for whole genome sequencing. WO2019/079656 discloses a method of DNA enrichment in which blocking oligonucleotides are used to suppress amplification of human (primarily mitochondrial) DNA. The blocking agents of WO2019/079656 are oligonucleotides conjugated to psoralen which is a linear furanocoumarin compound. When exposed to UV light it forms an adduct with the pyrimidine base thymine, thereby chemically-modifying non-target DNA into a form which is resistant to enzymatic extension. One drawback to this method is that the use of psoralen adds complexity, and the use of UV light is undesirable due to the introduction of an additional variable, the need for additional apparatus, and the ability of UV light to degrade nucleic acid including target nucleic acid.

The present invention provides, in various embodiments, an alternative method of blocking amplification of non-target sequences which utilises components of the CRISPR-Cas system. Cas9 proteins are disclosed in WO2021/075555 as having the ability to block polymerase chain reaction amplification, a process that is clearly distinct from the MDA required as a prerequisite to whole genome sequencing. MDA uses polymerases which are strand-displacing and highly progressive. They have the characteristic of "motoring" along the template DNA and have a strong tendency to displace any bound molecules including complementary DNA strands but also other molecules. For that reason, it is not sufficient for an amplification-blocking agent to merely bind ahead of an MDA strand-displacing polymerase, it must also meet the far more difficult technical requirement of remaining bound with sufficient tenacity to avoid being displaced by a strand displacing polymerase. Obviously, this requirement is met by covalently linked blocking agents (such as the psoralen adducts of WO2019/079656) but it is highly doubtful in the prior art as to whether blocking agents which are non-covalently associated with DNA will be bound with sufficient tenacity to resist being displaced by a highly progressive polymerase.

Φ29DNA polymerase (Φ29DNAP) is a strand-displacement polymerase which is a strong DNA-based motor able to perform strand displacement replication at a fast rate.

It is highly uncertain as to whether Cas9 is able to block Φ29DNA polymerase activity in real-world polymerisation reactions. Zhang et al. (2019) "The post-PAM interaction of RNA-guided SpCas9 with DNA dictates its target binding and dissociation". Science Advances 5: eeau9807, suggest that a catalytically dead Cas9 protein, dSpCas9, is unable to block Φ29DNA polymerase, whereas Zhang (2020) "Dynamics of *Staphylococcus aureus* Cas9 in DNA target association and dissociation" EMBO Reports Z: e50184 set-up a strand displacement assay using precise force-displacement spectroscopy ("optical tweezers") on a single molecule and discovered that under optimised conditions, which do not correspond to those encountered in a real amplification reaction, Φ29DNA polymerase is unable to dislodge a Cas9 protein. It may be that the difference between these data is accounted for by the use of different Cas9 proteins. Use of Cas proteins to block amplification typically employs catalytically dead Cas proteins (abbreviated to dCas). Catalytically dead Cas proteins may include dCas9 proteins. Catalytically dead Cas proteins are Cas proteins which have been mutated to lose their wild-type catalytic activity. For example, dCas9 is mutated to lose its endonuclease activity. Typically, this is achieved by introducing mutations in the endonuclease domains. It still retains its ability to bind to a target sequence via a guide RNA (sgRNA). The ease of designing and manufacturing sgRNAs to bind to specific targets makes dCas9 an attractive tool for targeting genetic loci and dCas9 has been used to target such loci for live cell imaging, and targeted gene activation or inactivation. Much of the prior art uses dCas9 from *Streptococcus pyogenes* (referred to as dSpCas9). The present invention is built in part on the realisation that unless covalent anchoring of the Cas protein is used (for example, by the production of psoralen adducts), dSpCas9 does not bind strongly enough to DNA sequences to avoid being displaced by a highly progressive strand displacement polymerase which, by its nature, has a strong tendency to displace molecules annealed ahead of it on its amplification target.

The present inventors have identified that, in a strand displacement reaction, dSaCas9 (catalytically dead Cas9 from *Staphylococcus aureus*), but not dSpCas9, binds strongly enough to resist dislodging by Φ29DNA polymerase.

Regardless of how the data of Zhang is to be understood, Zhang does not suggest that a Cas protein such as dSaCas9 and a strand-displacing polymerase such as Φ29DNA polymerase could be used together in a practical method of selectively amplifying DNA. A further reason for regarding the use of the combination of Φ29DNA polymerase and dSaCas9 as unlikely to be successful in suppressing non-target amplification in practice is "salt incompatibility" between the two proteins. Briefly, Na$^{2+}$ ions are required for Cas9 function and binding (Cas9 is typically used in a buffer containing 100 mM NaCl), whereas Φ29DNAP activity requires far lower salt concentrations (Φ29DNAP is typically used in a buffer containing 25 mM NaCl) which would be understood by a person skilled in the art as too low for Cas9 to bind to its target. The present invention is based, in part, on the surprising discovery that this "salt incompatibility" does not prevent the use of dSaCas9 to block non-target Φ29DNAP-mediated amplification in a multiple displacement amplification reaction, and that sufficient differential amplification of target sequence over non-target sequences occurs to permit the production of amplified and enriched DNA suitable for use in successful whole genome sequencing. This is surprising, because one would imagine that in light of the tremendous torque produced by a strand displacement polymerase such as Φ29DNAP, in order to resist displacement dSaCas9 would need to be optimally bound under optimal binding conditions. The present invention overcomes the salt-incompatibility issue by firstly binding the dSaCas9 protein under salt conditions optimised for dSaCas9 binding (typically about 100 mM NaCl). The invention is based on the surprising discovery that once that initial binding has occurred under optimal salt conditions, the salt concentration can then be changed to a concentration suitable for Φ29DNAP activity and that the bound sSaCas9 protein stays sufficiently well-bound to the non-target DNA template to block amplification of non-target species for long enough for the polymerase to significantly enrich the target DNA. This is surprising because salt ions are known to play an important role in stabilising the Cas9 protein and its constituent guide RNA and they might therefore be expected to be essential for maintenance of Cas9 binding (see, Nishimasu H, Cong L, Yan W X, Ran F A, Zetsche B, Li Y, Kurabayashi A, Ishitani R, Zhang F, Nureki O. "Crystal Structure of *Staphylococcus aureus* Cas9". Cell. 2015 Aug. 27; 162 (5): 1113-26. doi: 10.1016/j.cell.2015.08.007. PMID: 26317473; PMCID: PMC4670267). It is also surprising because weakened binding of dSaCas9 might be assumed to result in binding which is insufficiently strong to avoid displacement by a highly-progressive polymerase. Afterall, such a polymerase is understood to require strong binding of a blocking agent in order for it to be blocked as evidenced by the fact that it is able to displace dSpCas9.

Prior art methods of nucleic acid amplification and detection use Cas proteins and guide RNAs in various and imaginative ways. For example, EP4047091 discloses a method of discriminating between target and non-target nucleic acid during an isothermal amplification reaction. Essentially, the method employs the use of primers which hybridize to both target and non-target sequences. The amplification of non-target sequences is blocked by the use of a blocking agent. Various blocking agents are proposed including CpG methylation binding proteins and catalytically dead Cas proteins. Whilst dSpCas9 is proposed as a possible blocking agent (from a range of options), the "salt incompatibility" problems of using dSpCas9 with a strand-displacing polymerase are not addressed, nor is the fact that dSpCas9 is unable to bind sufficiently strongly to avoid being displaced by a highly progressive polymerase. The advantages of dSaCas9 over dSpCas9 and methods for overcoming salt incompatibility are not disclosed.

US2021/0040537 uses Cas complexes not to block amplification of a non-target sequence, but to bind it to a target sequence and thus protect it from degradation by an exonuclease prior to amplification. In such a set-up, the salt incompatibility issue does not arise and nor does the problem of displacement of the dSpCas9 disclosed by a highly progressive polymerase because the Cas complex and polymerase are not used together.

US2019/0085318 also uses a Cas complex, (for example, dSpCas9) to bind to a target, as opposed to non-target. After binding, target nucleic acid is enriched, for example, by binding the Cas complex to a particle such as a magnetic particle. Again, the potential problems of salt incompatibility between a Cas complex and a polymerase are not encountered, nor is the problem of dSpCas9 displacement by a highly progressive polymerase.

WO2020/006036 uses a Cas complex to selectively bind a target, as opposed to non-target, nucleic acid. Differential amplification of target versus non-target nucleic acid is achieved, not by blocking polymerase activity, nor by enrichment, but by using Cas complexes to introduce R-loop nucleic acid structures adjacent to the target sequence which can serve as a starting point for target sequence amplification.

US2019/0203280 uses a catalytically dead Cas complex to bind to a target sequence and produce an enhanced detection signal, for example, an increased resonant wavelength shift in a fluorescent detection.

SUMMARY OF INVENTION

According to a first aspect, the invention provides a method of selective DNA amplification of a DNA mixture comprising a first population of DNA and a second population of DNA, wherein:— a) a catalytically dead *Staphylococcus aureus* Cas complex (dSaCas9) comprising a dSaCas9 protein or derivative thereof complexed with one or more guide RNAs having selective binding affinity for DNA sequences preferentially present in the first population of DNA compared to the second population of DNA is contacted with the DNA mixture under a first reaction condition, said first reaction condition being suitable for binding of the dSaCas9 complex to DNA sequences for which it has a binding affinity, and then b) a strand-displacing DNA polymerase is contacted with the DNA mixture under a second reaction condition, said second reaction condition being suitable for amplification activity of the strand-displacing DNA polymerase.

According to a second aspect of the invention there is provided a kit comprising:

a first container containing catalytically dead *Staphylococcus aureus* dSaCas9 comprising dSaCas9 protein or derivative thereof complexed with one or more guide RNAs having selective binding affinity for one or more eukaryotic genomic DNA sequences, and a second container containing a strand-displacing DNA polymerase.

According to a third aspect of the invention there is provided use of catalytically dead *Staphylococcus aureus* Cas9 complex (dSaCas9) or a derivative thereof comprising one or more guide RNAs with selective binding affinities for DNA sequences preferentially present in the human, or other mammalian genome to inhibit selectively the amplification of said DNA sequences preferentially present in the human or other mammalian genome, in a DNA amplification reaction catalysed by a strand displacing DNA polymerase.

DRAWINGS

DETAILED DESCRIPTION OF INVENTION

Figure 1:
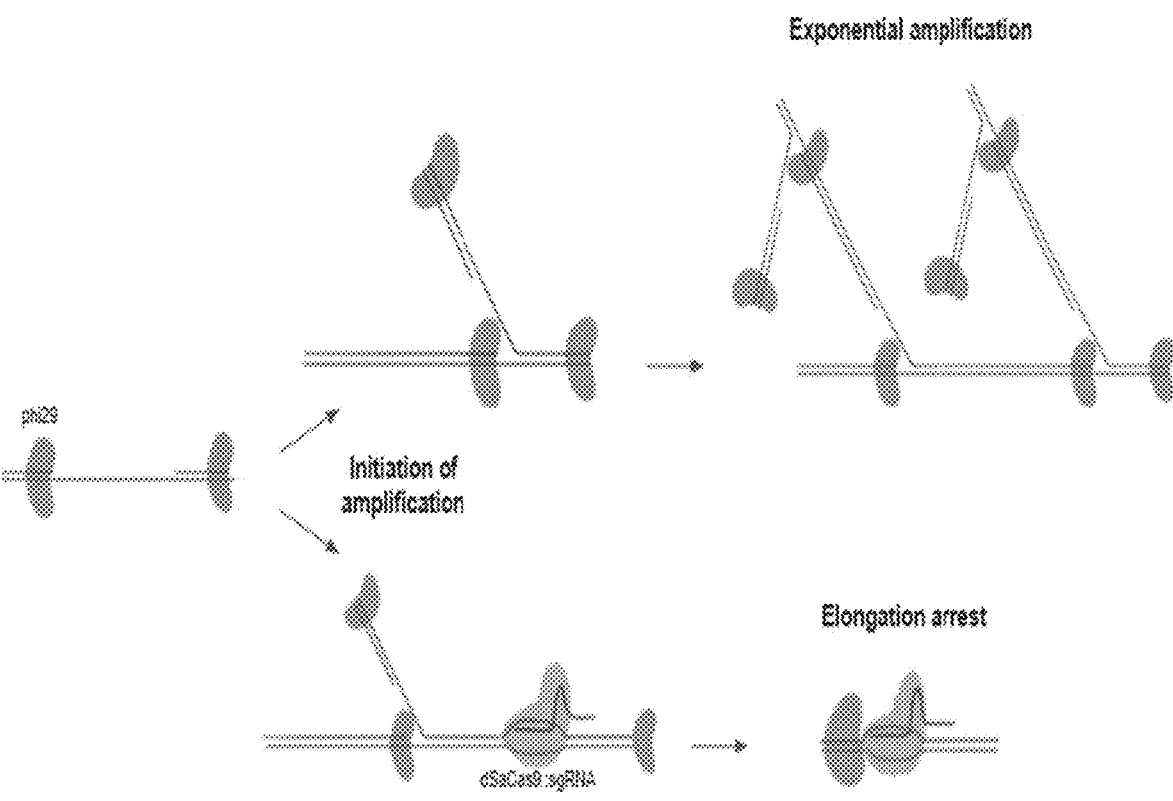
FIG. 1 is a diagrammatic illustration of dSaCas9 with guide RNA blocking strand displacement polymerisation of target DNA.

According to a first aspect, the invention provides a method of selective DNA amplification of a DNA mixture comprising a first population of DNA and a second population of DNA, wherein:— a) a catalytically dead *Staphylococcus aureus* Cas complex (dSaCas9) comprising a dSaCas9 protein or derivative thereof complexed with one or more guide RNAs having selective binding affinity for DNA sequences preferentially present in the first population of DNA compared to the second population of DNA is contacted with the DNA mixture under a first reaction condition, said first reaction condition being suitable for binding of the dSaCas9 complex to DNA sequences for which it has a binding affinity, and then b) a strand-displacing DNA polymerase is contacted with the DNA mixture under a second reaction condition, said second reaction condition being suitable for amplification activity of the strand-displacing DNA polymerase.

Selective Amplification

According to methods of the invention, the second population of DNA may be preferentially amplified relative to the first population of DNA. According to certain embodiments of all aspects of the invention, preferential amplification means application of the second population of DNA which is at least twice, or at least 3, 4, 5, 8 or 10 fold the amplification of the first population of DNA. Amplification may be measured by the copy number or total number of residues amplified (this latter measure approximates to total mass amplified).

First and Second Populations of DNA

The second population of DNA is preferably a population containing one or more pathogen DNA sequences. For example, one or more bacterial, fungal or viral DNA sequences (including cDNA sequences of RNA viruses, which have been produced by reverse transcription, such reverse transcription being an optional additional step of methods of the invention, optionally carried out prior to blocking and amplification steps). In certain embodiments the second population of DNA is a population of prokaryotic DNA. In certain embodiments DNA species comprise sequences of one or more of *Klebsiella pneumonia, Acinetobacter baumannii, Pseudomonas aeruginosa, Enterobacter* sp. *Staphylococcus aureus*, and *Enterococcus fecium*. The first population of DNA is preferably a population containing one or more eukaryotic DNA sequences in particular mammalian sequences, in particular human sequences. According to some embodiments, the first population contains one or more human chromosomal sequences. Additionally, or alternatively, the first population contains one or more human mitochondrial sequences. In certain preferred embodiments, the first population contains both human chromosomal sequences and human mitochondrial sequences.

Dna Mixture

The DNA mixture of the invention may be, or be derived from, a human blood sample, such as a human blood sample extracted from a subject suspected of having a pathogen infection, for example a bacterial infection, for example sepsis. In other embodiments the DNA mixture may be derived from an alternative human tissue such as, blood, plasma, lymph, solid tissue (for example a solid tissue biopsy, or ex vivo sample), pus, mucus, semen, amniotic fluid, cerebrospinal fluid, urine or faecal matter. The DNA mixture is preferably pre-processed prior to use in a method of the invention (alternatively pre-processing steps may optionally be regarded as additional steps of a method of the invention). Pre-processing may include one or more of removal or depletion of eukaryotic cells (for example removal or depletion of human red and white blood cells from a sample of human blood, or removal of sperm cells and leukocytes from a sample of semen). Such removal or depletion may be carried out by any suitable method including centrifugation, settling or filtration. Pre-processing may additionally (for example subsequently) or alternatively include cell lysis and/or killing or inactivation of potentially intact cells or pathogens).

Optionally, the DNA mixture contains an overwhelming amount of the first population of DNA versus the second population of DNA (measured by total amount by weight and/or copy number). For example, the first population may be present in at least 100, 1000, 1000 or 100,000 times the amount of the second population.

Catalytically Dead Cas Complexes (dCas)

"Catalytically dead" in the context of a Cas complex means lacking Cas enzymatic activity (i.e., enzymatic activity is completely or substantially abolished, for example by site-specific sequence changes, so as not to interfere with the assay). The catalytically dead Cas complex comprises a catalytically dead Cas protein or derivative thereof and one or more guide RNAs. According to the presently claimed invention, the catalytically dead Cas protein or derivative thereof is catalytically dead *S. aureus* Cas9 (dSaCas9) or derivatives thereof. In certain alternative embodiments of this disclosure but not the presently-claimed invention the catalytically dead Cas protein is catalytically dead *S. aureus* Cas12 (dSaCas12) or derivatives thereof. In certain embodiments this disclosure, not currently claimed, encompasses catalytically dead *S. aureus* Cas12 (dSaCas12a) or derivatives thereof. In certain embodiments the disclosure encompasses catalytically dead *S. aureus* Cas14 (dSaCas14) or derivatives thereof.

The sequence of dSaCas9 is given below:

```
                                    (SEQ ID NO.: 1)
MSDKIIHLTDDSFDTDVLKADGAILVDFWAEWCGPCKMIAPILDEIAD

EYQGKLTVAKLNIDQNPGTAPKYGIRGIPTLLLFKNGEVAATKVGALS

KGQLKEFLDANLAGSGSGHMHHHHHHSSGLVPRGSGMKETAAAKFERQ

HMDSPDLGTDDDDKMPKKKRKVEASMKRNYILGLAIGITSVGYGIIDY

ETRDVIDAGVRLFKEANVENNEGRRSKRGARRLKRRRHRIQRVKKLL

FDYNLLTDHSELSGINPYEARVKGLSQKLSEEEFSAALLHLAKRRGVH

NVNEVEEDTGNELSTKEQISRNSKALEEKYVAELQLERLKKDGEVRGS

INRFKTSDYVKEAKQLLKVQKAYHQLDQSFIDTYIDLLETRRTYYEGP

GEGSPFGWKDIKEWYEMLMGHCTYFPEELRSVKYAYNADLYNALNDLN

NLVITRDENEKLEYYEKFQIIENVFKQKKKPTLKQIAKEILVNEEDIK

GYRVTSTGKPEFTNLKVYHDIKDITARKEIIENAELLDQIAKILTIYQ
```

-continued

```
SSEDIQEELTNLNSELTQEEIEQISNLKGYTGTHNLSLKAINLILDEL

WHTNDNQIAIFNRLKLVPKKVDLSQQKEIPTTLVDDFILSPVVKRSFI

QSIKVINAIIKKYGLPNDIIIELAREKNSKDAQKMINEMQKRNRQTNE

RIEEIIRTTGKENAKYLIEKIKLHDMQEGKCLYSLEAIPLEDLLNNPF

NYEVDHIIPRSVSFDNSFNNKVLVKQEEASKKGNRTPFQYLSSSDSKI

SYETFKKHILNLAKGKGRISKTKKEYLLEERDINRFSVQKDFINRNLV

DTRYATRGLMNLLRSYFRVNNLDVKVKSINGGFTSFLRRKWKFKKERN

KGYKHHAEDALIIANADFIFKEWKKLDKAKKVMENQMFEEKQAESMPE

IETEQEYKEIFITPHQIKHIKDFKDYKYSHRVDKKPNRELINDTLYST

RKDDKGNTLIVNNLNGLYDKDNDKLKKLINKSPEKLLMYHHDPQTYQK

LKLIMEQYGDEKNPLYKYYEETGNYLTKYSKKDNGPVIKKIKYYGNKL

NAHLDITDDYPNSRNKVVKLSLKPYRFDVYLDNGVYKFVTVKNLDVIK

KENYYEVNSKCYEEAKKLKKISNQAEFIASFYNNDLIKINGELYRVIG

VNNDLLNRIEVNMIDITYREYLENMNDKRPPRIIKTIASKTQSIKKYS

TDILGNLYEVKSKKHPQIIKKG*
```

Binding Affinity and sgRNA

In the context of Cas complexes, guide RNA, also referred to as "single guide RNA" or "sgRNA" is a short piece of RNA which is designed for binding the Cas complex of which it is part to a specific nucleic acid sequence. It achieves this by having a region which is complementary to a specific nucleic acid sequence (the guide or guiding region). It also has other regions which are important for the other functions of the sgRNA including the ability to complex with the Cas protein. The design of sgRNA sequences is well understood by those skilled in the art meaning that it is a matter of routine to design a sgRNA which is capable of recognising virtually any nucleic acid sequence in a sequence specific way whilst also having other functions required for the sgRNA to form part of the Cas complex. A recent review of sgDNA design, including strategies for ensuring good specificity and reducing off targeting may be found in Manghwar, Hakim; Li, Bo; Ding, Xiao; Hussain, Amjad; Lindsey, Keith; Zhang, Xianlong; Jin, Shuangxia 2020. CRISPR/Cas Systems in Genome Editing: Methodologies and Tools for sgRNA Design, Off-Target Evaluation, and Strategies to Mitigate Off-Target Effects. Advanced Science, Vol. 7 (6), p. 1902312-n/a, Article 1902312.

Derivatives

Derivatives include equivalent compounds with substantially the same properties as the parent molecule so as to be able to function in methods of the invention. Derivatives include naturally-occurring and artificially-generated mutants or variants of wild type Cas proteins according to the invention.

According to certain embodiments the dSaCas9 proteins relating to the invention comprise a peptide sequence that is at least 80%, at least 85%, at least 90% or at least 95% identical (in a BLAST algorithm comparison) to the dSaCas9 sequence recited above.

The guide RNA (sgRNA) comprises a sequence with binding affinity for the sequences preferentially present in the first population of DNA, for example with binding affinity for sequences preferentially present in eukaryotic DNA, for example with binding affinity for eukaryotic genomic DNA sequences (at one or more sites to allow for total or at least sufficient blocking of unwanted DNA). In certain embodiments this binding affinity results from complete complementarity with the eukaryotic genomic DNA sequence. However, the invention will tolerate a level of sequence mis-match provided that the binding affinity is still substantially selective for sequences preferentially present in the first DNA population, for example eukaryotic DNA sequences. The sgRNA also comprises a sequence for association with the protein component of Cas9.

In preferred embodiments catalytically dead dSaCas9 complexes or derivatives thereof, of the invention comprise multiple sgRNA molecules collectively having binding affinities for multiple eukaryotic DNA sequences for example multiple sgRNA molecules collectively having binding affinities for multiple human DNA sequences. Preferably these DNA sequence are DNA sequences which are not present in pathogen DNA or at least not present in the DNA of pathogens of interest.

Source and Sequences of First DNA Population

The first DNA population may preferably be a population comprising eukaryotic DNA sequences. Eukaryotic DNA sequences according to the invention include sequences which are present in eukaryotic DNA, but which are not present (or are present at materially lower incidence) in non-eukaryotic DNA.

An illustrative example of a eukaryotic sequence which is not present in non-eukaryotic is the human CCDC88a gene. The guide RNAs of the dSaCas9 complex are each designed so as to include short sequence (typically about 22 residues) complementary to either strand of DNA present in the first DNA population, but which are not present in the second DNA population.

Illustrative examples of sequences found in eukaryotic DNA but absent in pathogen DNA include the following sequences taken from the human CCDC88a gene:

```
1.
                            (SEQ ID NO.: 2)
GCGCGGCGGUGAUUUUGUGCC 2.
                            (SEQ ID NO.: 3)
AUUGGGAGCAGUUUCGCUGGU 3.
                            (SEQ ID NO.: 4)
GUCCGUCGUCGAAGCCACUUCU
```

Guide RNA according to the invention will preferably meet further criteria (which may be referred to as guide RNA design rules) in order to effectively function as guide RNA molecules. For example, guide RNA may meet the following rules:

1. The presence of a Protospacer Adjacent Motif (PAM) appropriate for the catalytically dead SaCas9 protein which it is to be used with. For example, a dSaCas9 PAM sequence is NNGRRT).
2. The presence, upstream of the PAM sequence, of a sequences consisting of ~21-22 nucleotides selected to be complementary to either strand of DNA present in the second DNA population
3. A guanine may optionally be added to the 5' end of the sequence to enable better transcription by a U6 promoter and thus higher yield of the sgRNA during its production, and
4. The presence of additional Cas scaffold sequence e.g.
5   GUUUUAGUACUCUGGAAACAGAAUCUAC-

UAAAACAAGGCAAAAUGCCGUGUU UAUCUC-GUCAACUUGUUGGCGAGAUUU 3' (SEQ ID NO.: 5)

Steps of Method

According to the first aspect of the invention, step a) of the method is carried out before step b). By carrying out the steps sequentially the first reaction condition may differ from the second reaction condition. In certain "sequential" embodiments, the first reaction condition may optionally have a relatively high salt concentration and the second reaction condition may optionally have a relatively low concentration. By carrying out step b) after step a), the strand-displacing DNA polymerase may be provided in a solution capable of lowering the free salt concentration by diluting and/or sequestering salt. Alternatively, salt concentration may be lowered between steps a) and b) by using dialysis to reduce the salt concentration. For example, the method may be carried out in contact with a dialysis membrane with a suitable exclusion cut off (MWCO of 2000 or so). Exchange of a dialysis buffer may be carried out to promote salt reduction.

Dna Polymerase

The invention relates in all aspects to a DNA polymerase that is a strand-displacing DNA polymerase. By this is meant any DNA polymerase favourably applicable to multiple displacement amplification (MDA) suitable for whole genome amplification (optionally to prepare DNA suitable for whole genome sequencing). Preferably the polymerase is of high fidelity allowing it to accurately amplify single nucleotide polymorphisms (SNPs) for subsequent detection. Φ29DNA polymerase and derivatives thereof are especially suitable strand-displacing DNA polymerases for use with the invention. Derivatives in this context relate to equivalent enzymes with substantially the same properties of Φ29DNAP so as to be able to function in methods of the invention. Derivatives include naturally-occurring and artificially-generated mutants or variants of wild type Φ29DNAP. Wild type 29DNAP has the sequence given below:

```
Bacillus phage Φ 29 DNA polymerase
                            (SEQ ID NO.: 6)
MKHMPRKMYSCDFETTTKVEDCRVWAYGYMNIEDHSEYKIGNSLD

EFMAWVLKVQADLYFHNLKFDGAFIINWLERNGFKWSADGLPNTY

NTIISRMGQWYMIDICLGYKGKRKIHTVIYDSLKKLPFPVKKIAK

DFKLTVLKGDIDYHKERPVGYKITPEEYAYIKNDIQIIAEALLIQ

FKQGLDRMTAGSDSLKGFKDIITTKKFKKVFPTLSLGLDKEVRYA

YRGGFTWLNDRFKEKEIGEGMVFDVNSLYPAQMYSRLLPYGEPIV

FEGKYVWDEDYPLHIQHIRCEFELKEGYIPTIQIKRSRFYKGNEY

LKSSGGEIADLWLSNVDLELMKEHYDLYNVEYISGLKFKATTGLF

KDFIDKWTYIKTTSEGAIKQLAKLMLNSLYGKFASNPDVTGKVPY

LKENGALGFRLGEEETKDPVYTPMGVFITAWARYTTITAAQACYD

RIIYCDTDSIHLTGTEIPDVIKDIVDPKKLGYWAHESTFKRAKYL

RQKTYIQDIYMKEVDGKLVEGSPDDYTDIKFSVKCAGMTDKIKKE

VTFENFKVGFSRKMKPKPVQVPGGVVLVDDTFTIK
```

According to certain embodiments Φ29DNAP derivatives relating to the invention are at least 80%, at least 85%, at least 90% or at least 95% identical (in a BLAST algorithm comparison to the wild-type Φ29DNAP sequence given above).

First and Second Conditions

The invention is based on the realisation that dSaCas9 is able to fulfil its blocking function (and thereby facilitate differential amplification of a target sequence over a non-target sequence) even under conditions which are optimal for a strand displacement DNA polymerase but which are not optimal for dSaCas9 binding providing that the dSaCas9 has been previously allowed to bind to non-target DNA under conditions which are more optimal for dSaCas9 to bind. Expressed in the language used in the claimed invention, there are two reaction conditions, a first reaction condition, said first reaction condition being suitable for binding of the dSaCas9 complex to DNA sequences for which it has a binding affinity, and then a strand-displacing DNA polymerase is contacted with the DNA mixture under a second reaction condition, said second reaction condition being suitable for amplification activity of the strand-displacing DNA polymerase. Preferably, the first and second reaction conditions are different. In preferred embodiments the first and second reaction conditions have different salt concentration. For example, at least a 2, 3 or 4 fold difference in molar concentration of NaCl.

Salt Concentrations

The invention in certain embodiments recites a relatively high free salt concentration in a first reaction mixture and a relatively low free salt concentration in the second reaction mixture.

In the present application, "salt concentration" describes the concentration of salt ions free to coordinate with the DNA polymerase (for example strand displacement DNA polymerase) and/or the dSaCas9 or derivative thereof. Ions which are present but unable to coordinate with such compounds, because, for example they are chelated, precipitated or sequestered do not contribute to the free high or low salt concentration as defined by the present application and therefore it can be understood that changes in free salt concentration such as that required in the first aspect of the invention may be achieved via dilution and/or by the addition of a chelating or precipitating agent or a sequestering agent. Accordingly the second reaction mixture may optionally lower the free salt concentration of the first reaction mixture when added to it by simple dilution or because the second reaction mixture contains a chelating agent or a precipitating agent. Alternatively, as discussed above, a dialysis arrangement may be employed to reduce salt concentration as described above. In preferred embodiments "salt concentration" refers to NaCl concentration.

Examples of Relatively High and Low Free Salt Concentrations

As an example, a relatively low salt concentration is an NaCl concentration below 50 mM, for example 10 mM to 50 mM, for example 15 mM to 40 mM, for example 18 mM to 30 mM, for example 22 mM to 28 mM, for example about 25 mM.

As an example, a relative high salt concentration is an NaCl concentration above 50 mM, for example 50 mM to 200 mM, for example 50 mM to 180 mM, for example 60 mM to 160 mM, for example 70 mM to 150 mM, for example 75 mM to 130 mM, for example 80 mM to 120 mM, for example 90 mM to 110 mM for example about 100 mM.

Optionally, the first container may further contain a relatively high salt concentration and the second container may further contain a relatively low salt concentration and be capable of lowering the free salt concentration (for example by dilution and/or sequestration) of the first container when added to the first container, by a factor of at least a half.

Temperatures of First and Second Reaction Conditions

According to certain embodiments of methods of the invention, the first reaction condition and the second reaction condition are of different temperatures. For example, the first reaction condition may be between 32 and 40° C. (for example, between 35 and 38° C., for example about 37° C.). For example, the second reaction condition may be between 25° C. and 32° C. (for example, between 27° C. and 32° C., for example, between 29° C. and 31° C., for example, about 30° C.). In certain embodiments, the first reaction condition may be between 32° C. and 40° C. (for example, between 35° C. and 38° C., for example about 37° C.) and the second reaction condition may be between 25° C. and 32° C. (for example, between 27° C. and 32° C. for example, between 29° C. and 31° C., for example, about 30° C.). Such temperature ranges may be preferred when the invention is used with a DNA polymerase with an optimum operating temperature of about 30° C. However, there are available strand-displacing DNA polymerases suitable for use in the invention with higher operating temperatures, for example those having optimal operating temperatures of above 30° C. including those having optimum operating temperature of up to about 45° C. Accordingly, the invention includes embodiments wherein the second reaction condition may be between 32° C. and 50° C. (for example, between 4° and 50° C., for example about 45° C.) In certain embodiments, the second reaction condition may be between 32° C. and 50° C. (for example, between 40° C. and 50° C., for example about 45° C.) and the first reaction condition may be between 32° C. and 40° C. (for example, between 35° C. and 38° C., for example about 37° C.). Such temperature ranges may be preferred when the invention is used with a DNA polymerase with an optimum operating temperature of about 45° C.

According to certain preferred embodiments, it is preferred that the first and second reaction conditions comprise a combination of both the preferred temperature conditions described above in combination with the preferred salt concentrations described above.

Timing of Method Steps

According to the methods of the invention there are at least two method steps, step a) (carried out under a first reaction condition) and step b) (carried out under a second reaction condition). In this aspect of the invention step a) is characterized as comprising contacting dSaCas9 with the DNA mixture and step b) is characterised as comprising contacting the strand-displacing DNA polymerase with the DNA mixture. It is to be noted that step a) does not preclude the presence of the strand-displacing DNA polymerase nor contact between the strand-displacing DNA polymerase and the DNA mixture and step b) does not preclude the presence of dSaCas9 nor contact between the dSaCas9 and the DNA mixture. The key difference between the two steps is that step a) is carried out under a first reaction condition and step b) is carried out under a second reaction condition. Preferably the first reaction condition and the second reaction condition are different. In preferred embodiments they differ in respect of their free salt concentration by a factor of at least 2, 3 or 4, they may also optionally differ in their temperatures. In certain embodiments step a) may last for between 30 minutes and 6 hours, for example between 45 minutes and 4 hours, for example between 1 and 3 hours.

Accordingly, in preferred embodiments of methods of the invention in step a) a catalytically dead *Staphylococcus aureus* Cas9 complex (dSaCas9) comprising a dSaCas9 protein or derivative thereof complexed with one or more guide RNAs having selective binding affinity for DNA sequences preferentially present in the first population of DNA compared to the second population of DNA is contacted with the DNA mixture in the presence of the strand-displacing DNA polymerase of step b) under a first reaction condition, said first reaction condition being suitable for binding of the dSaCas9 complex to DNA sequences for which it has a binding affinity, and in step b) a strand-displacing DNA polymerase is contacted with the DNA mixture in the presence of the dSaCas9 of step a) under a second reaction condition, said second reaction condition being suitable for amplification being suitable for amplification activity of the strand-displacing DNA polymerase.

Repetition of Steps and "Salt Cycling"

According to methods of the invention step a) is carried out followed by step b) being carried out. This does not preclude any or both of the steps being repeated. For example, step a) may be carried out followed by step b), followed by a repeat of step a) followed by a repeat of step b). For example, step b) may be carried out followed by step a), followed by a repeat step b). It would normally be preferred to finish a method of the invention with step b) because that is the amplification step, but the invention does not preclude methods finishing on step a). In certain embodiments, steps a) and b) may be cycled through at least twice, at least thrice or at least 4 or 5 times. According to certain preferred embodiments, step b) is carried out for at least 45 minutes (for example, for between 45 minutes and 4 hours, for example, for about 1 hour) at 30° C. (or if a high temperature polymerase is used 45° C.) at 25 mM NaCl, followed by step a) for between 5 and 30 minutes (for example for about 15 minutes) at 37° C. at 100 mM NaCl, followed by b) carried out for at least 45 minutes (for example, for between 45 minutes and 4 hours, for example, for about 3 hours) at 30° C. (or if at high temperature polymerase is used 45° C.) at 25 mM NaCl. Optionally, steps a) and then step b) may be repeated once, twice, thrice or 4 or 5 times more.

Changing between steps a) and b) and changing between steps b) and a) involves a change in reaction condition, for example, from the first reaction condition to the second reaction condition, and/or from the second reaction condition to the first reaction condition. This change may comprise a change in temperature and/or a change in free salt concentration. In certain preferred embodiments it comprises a change in both the temperature and the free salt concentration. Changes in temperature may be provided by carrying out the method in a reaction container on a heating or cooling block or by transferring the reaction container from one temperature to another (for example from one water bath or heating block to another). Increases in free salt concentration may be provided by any means for example by the addition of salt, or the removal of water or addition of salt (for example by dialysis). Decreases in free salt concentration may be provided by any suitable means for example by the dilution of reactants with a solution having a relatively low salt concentration, or by the addition of a salt sequestering or chelating agent or by addition of water or removal of salt by dialysis.

Further Method Steps

Methods of the invention optionally include additional steps in certain embodiments. For example, preceding the recited steps of the first aspect of the invention there may optionally be one or more additional steps of preparing the DNA mixture from a sample, such as a sample taken from a human subject. There may optionally be additional steps of obtaining the sample for example taking the sample from the subject. The subject in such circumstances may optionally be, in certain embodiments, a human, for example a human suffering from, or suspected to be suffering from a disease, disorder or infection, especially a bacterial infection, especially bacterial sepsis.

Methods of the invention optionally include one or more additional steps that proceed the recited steps of the first aspect of the invention. Such steps may optionally include sequencing the selectively-amplified DNA. It is especially preferred that the selectively-amplified DNA is subjected to genome sequencing in which a substantial majority or all of the genome of an organism (for example more than 60, 70, 80 or 90%) is sequenced.

Subsequent to genome sequencing the sequence data may optionally be analysed (for example by sequence comparison software) in order to detect (and identify) any bacterial organism present (and optionally to identify relevant phenotype features including drug susceptibility, toxin production, antibiotic resistance properties and virulence factors). The method of the invention may optionally include treating the subject for a bacterial infection (for example by administering an antibiotic or other anti-infective or therapeutic drug). The method of the invention may optionally include treating the subject for a viral infection (for example by administering an antiviral therapeutic agent or other therapeutic drug). The method of the invention may optionally include treating the subject for a fungal infection (for example by administering an antifungal agent or other therapeutic drug).

Optionally, the subject may already be subject to treatment for a bacterial, viral or fungal infection or suspected, viral or fungal bacterial infection and the method of the invention is used to monitor the progress and effectiveness of that treatment or optionally to change or cease a treatment of a subject that is already underway.

Enrichment Parameters

Selective amplification is a process wherein one DNA population is amplified to a greater extent than another DNA population. According to the present invention the second population of DNA is selectively amplified ("enriched") relative to the first population of DNA. That does not necessarily mean that the result of the method of the invention is a mixture of the first and second DNA populations in which there is a greater amount (as assessed by total weight, qPCR, sequencing or copy number) of the second population than there is of the first population, merely that the copy number of the second population has been increased by a larger factor than has the copy number of the first population from the amount present in the pre-amplification sample. The difference between the increase in the copy number of the second population and the increase in the copy number of the first population may be taken as the enrichment factor. The enrichment factor is preferably at least 4, at least 6, at least 8, at least 10, at least 15, at least 20, at least 50 or at least 100.

Kits of the Invention

According to a second aspect of the invention there is provided a kit comprising:

a first container containing catalytically dead *Staphylococcus aureus* Cas9 complex (dSaCas9) comprising a dSaCas9 protein or derivative thereof complexed with one or more guide RNAs, with selective binding affinity for one or more eukaryotic genomic DNA sequences, and a second container containing a DNA polymerase.

In certain embodiments the first container contains catalytically dead dSaCas9 or a derivative thereof comprising guide RNAs with selective binding affinity for one or more eukaryotic genomic DNA sequences and a relatively high salt concentration, and the second container contains a DNA polymerase, such as a strand-displacing DNA polymerase, and a relatively low free salt concentration, wherein the contents of the second container is capable of lowering the free salt concentration in the first solution when added to the first solution by a factor of at least one half.

According to certain embodiments, kits of the invention may comprise dialysis equipment to lower and/or raise the free salt concentration of a solution.

Kits of the second aspect of the invention are adapted for carrying out methods in accordance with the first aspect of the invention. They may optionally include instructions reciting the steps of the first aspect of the invention. Kits of the invention may optionally include a dialysis device as described herein, optionally having a molecular cut off as described above. It is to be understood that features described above as preferred embodiments of the method of the first aspect of the invention, are also preferred features of kits of the second aspect of the invention. For example, features of the dSaCas9 or derivative thereof, guide RNAs, eukaryotic genomic sequences, salt concentrations, changes in salt concentration, temperatures, changes in temperatures, repetition of steps, features of the strand displacing DNA polymerase described above in relation to the first aspect may also be applicable to the second aspect.

Kits of the invention comprise a first and second container. These containers may contain sufficient quantities for multiple implementations of the method of the invention to take place. In other embodiments the first and second containers contain sufficient quantities of reagent for a single selective amplification reaction.

Containers of the invention may contain reagents in solution or in lyophilised or another immobilised form requiring activation by addition of water. If the containers are provided in a form wherein the reagents require addition of water (or other aqueous solution) before use, it is to be understood that the references in the definition of the invention to relatively high and relatively low free salt concentrations, refer to the salt concentrations achieved following addition of water (or other aqueous solution) in accordance with the instructions provided with the kit.

Containers may be provided in a kit of the invention in multiple, for example in multiple single reaction quantities. They may be provided in a box or outer packaging, for example with instructions and optionally other reagents or equipment for carrying out optional additional steps (for example those steps described above as optional "preceding" or "proceeding" steps) of the first aspect of the invention).

According to a third aspect of the invention there is provided use of catalytically dead *Staphylococcus aureus* Cas9 (dSaCas9) complex or a derivative thereof and one or more guide RNAs with selective binding affinities for DNA sequences preferentially present in the human or other mammalian genome, to inhibit selectively the amplification of said DNA sequences preferentially present in the human or other mammalian genome, in a DNA amplification reaction catalysed by a DNA polymerase for example a strand-displacing DNA polymerase.

Use according to the third aspect of the invention may optionally comprise use of a kit of the second aspect of the invention (as may the method of the first aspect of the invention). It is to be further understood that preferred or optional features of embodiments described above in relation to the first or second aspect of the invention, may, where appropriate, be applicable to optional embodiments of the third aspect of the invention. For example, features of the dSaCas9 or derivative thereof, guide RNAs, human genomic sequences, free salt concentrations, changes in free salt concentration and strand displacing DNA polymerase described above in relation to the first aspect may also be applicable to the second aspect.

Use according to the third aspect of the invention may optionally be use for enrichment of any prokaryotic DNA present (or suspected of being present) in a sample (for example a sample as described above in relation to other aspects of the invention) relative to any eukaryotic DNA present (or suspected of being present) in the sample. For example, use of the third aspect of the invention may be for the enrichment of any bacterial DNA present (or suspected or being present) in a sample taken from a human subject prior to whole genome amplification of any bacterial DNA present.

EXAMPLES

The following non-limiting examples are presented below to illustrate how the invention may be implemented and to demonstrate its utility.

Theoretical Explanation of Blocking of Amplification

FIG. 1 shows diagrammatically a theoretical understanding of the background and principle behind the invention. The drawings at the top of the page show the control condition in which there is no blocking of amplification. This is the situation in respect of prokaryotic DNA which is not blocked. As can be seen from those drawings, the polymerase binds to the DNA and extends a primer. For clarity, the first drawing does not show the target DNA as double stranded which it would usually be. This means that as the primer is extended as a nascent strand of the double stranded DNA ahead of the primer (the non-template strand) is displaced. This feature is shown in the second drawing which also shows that amplification can occur at multiple sites on the template.

The bottom drawings show diagrammatically how in accordance with the invention, if a dSaCas9 protein is encountered, it can block strand displacement and amplification. It should be noted that the binding of the dSaCas9 involves the participation of the guide RNA (sgRNA) which can be made specific for sequences to be targeted by the dSaCas9 and thereby not amplified.

Materials and Methods dSaCas9 Expression and Purification

A DNA sequence of the catalytically inactive Cas9 of *Staphylococcus aureus* (known as dSaCas9) was identified and cloned into a plasmid based on the pET system with an internal his-tag, using the Golden Gate cloning methodology. Successful cloning was confirmed with PCR+Sanger sequencing and the protein expressed overnight in Terrific broth in BL21 (DE3) cells. The pellet was frozen until further use at −20° C. The pellet was then resuspended in lysis buffer (20 mM Tris-HCl, 150 mM NaCl, 5 mM Imidazole, 5 mM MgCl2, ~1 mg DNase, 1× SIGMA-FAST™ Protease Inhibitor Cocktail) and the protein liberated by sonication. The protein was then purified sequentially by His-column and cation-exchange chromatography using the methods of Teng, Allen C. T., Marjan Tavassoli, Suja Shrestha, Kyle Lindsay, Evgueni A Ivakine, Ronald Cohn, J. Paul Santerre and Anthony O. Gramolini. "An Efficient and Cost-effective Purification Methodology for SaCas9 Nuclease." bioRxiv (2021): n. pag. which were adapted to be used with a NGC liquid chromatography system. The protein was concentrated using an Amicon-15 10K NMWL column and buffer exchanged into the same storage buffer as used by Zhang et al. (20 mM Tris-HCl, pH 7.5, 500 mM KCl, and 1 mM DTT) at −80° C.

Blocking Assay

Template DNA for all reactions consisted of two plasmids denoted Template A and Template B. These plasmids contained the same backbone but had distinct coding regions. ~0.01 ng of Template A and B were mixed with random hexamers (Thermofisher) to a 1.5 mM final concentration. The template-random hexamer mix was incubated at 95° C. for 3 min to denature the template DNA and left on ice for 5 min to allow for random hexamer incorporation within the reannealed double-stranded DNA. sgRNA targeted against the coding region of Template A was incubated with dSa-Cas9 at a ratio of 20:1 (sgRNA:dSaCas9) in reaction buffer (50 mM Tris-HCl pH 8.0, 100 mM NaCl, 10 mM MgCl2) at 37° C. for 15 min with shaking at 400 RPM in a Thermomixer to produce the sgRNA::dSaCas9 complex. The sgRNA::dSaCas9 complex was then incubated for 30 min at 37° C. with shaking at 400 RPM at a molar ratio of ~55:1 with the template-random hexamer mixture. Phi29 (NEB) master mix was prepared according to the manufacturer's instructions and added to the sgRNA::dSaCas9-template DNA mixture. The master mix was added in such volumes to give a final NaCl concentration of 24.8 mM. DNA was then amplified at 30° C. for 1 hr. At this point NaCl was added to a final concentration of 100 mM along with an additional 5 μl of 70 nM sgRNA::dSaCas9 and the reaction incubated for 15 min at 37° C. Phi29 (NEB) master mix was then added, bringing the NaCl concentration down to 25 mM and the reaction incubated at 30° C. for a further 3 hr. Phi29 was then inactivated by incubation at 65° C. and the relative quantities of Template A/B determined by qPCR.

qPCR

Singleplex quantitative qPCR was performed using TaqMan Advanced Fast master mix and primer/probes designed against Template A (with an incorporated FAM probe) or B (HEK/VIC probe). Relative DNA concentrations were determined against a standard curve performed on each qPCR plate, against either Template A or B. qPCR was performed with at least two technical replicates, using the QuantStudio 5.

Results

Figure 2:
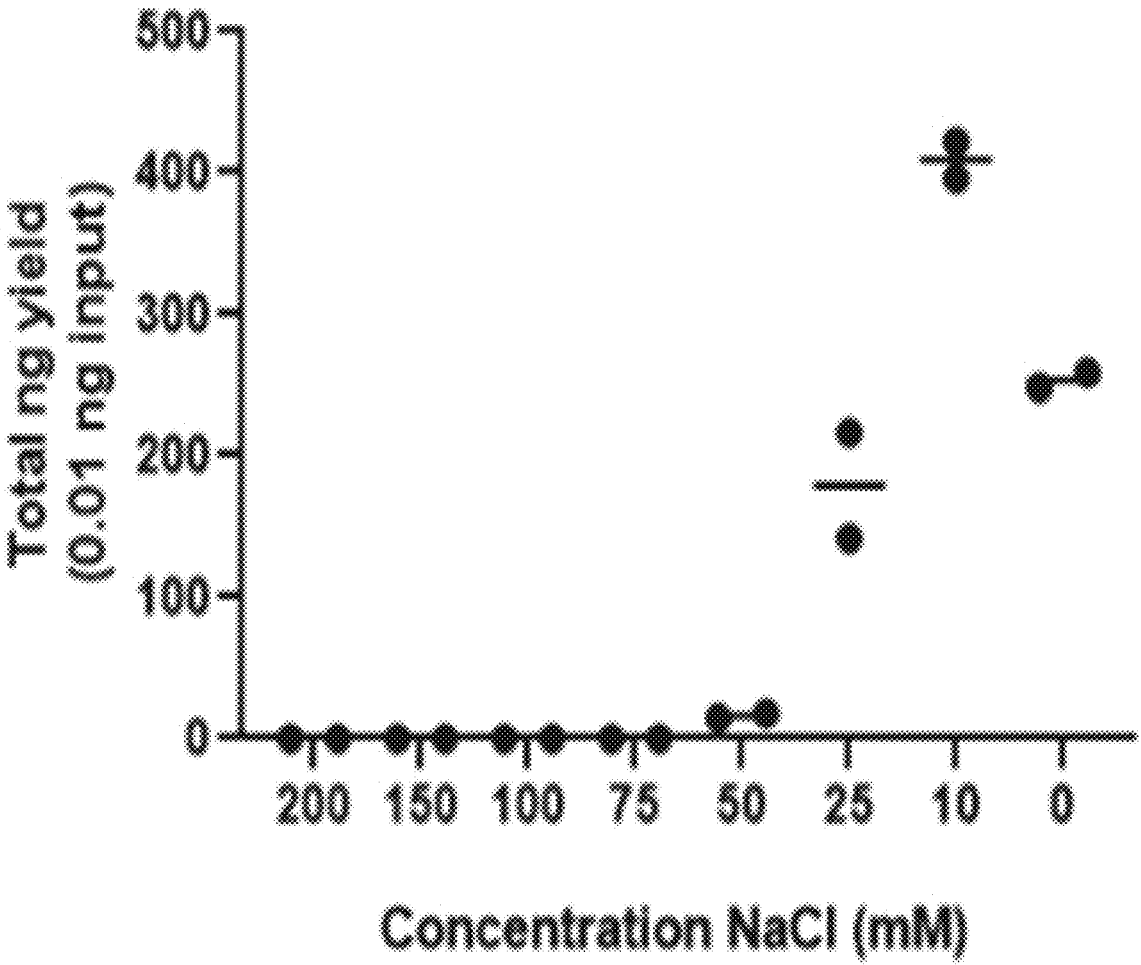
FIG. 2 shows the results of an experiment to determine the salt tolerance of @DNA polymerase ($\Phi$29DNAP)

As previously described, dSaCas9 requires Na+ ions to effectively bind target DNA, which has led previous work to use NaCl concentrations of 100 mM (Zhang et al., 2020). Contrastingly, phi29 has a potent sensitivity to NaCl (FIG. 2) which prevents it from being used at concentrations higher than 25 mM, as shown in FIG. 2 which is an experimental determination of NaCl tolerance of WT phi29 (NEB).

Reactions performed as described in materials and methods using a 0.01 ng input of Template B with varying concentrations of NaCl. To deal with this, as described in the materials and methods section, we sequentially altered the NaCl concentration in the reaction (by adding NaCl or diluting the reaction) to facilitate both dSaCas9 binding and phi29 amplification in the same tube. Reactions were performed where a DNA mixture of Template A/B was incubated either alone, with the dSaCas9::sgRNA complex (sgRNA targeted against Template A), or with dSaCas9 only. As shown in FIG. 3A, the presence of the dSaCas9::sgRNA complex results in 7.1 and 3.9 fold reductions in Template A amplification compared to the sgRNA-only and null dSaCas9/sgRNA controls respectively. Importantly, amplification of Template B is not affected by exposure to the dSaCas9::sgRNA complex, and may in fact be slightly beneficial (1.1 and 1.2 fold increase in Template B amplification relative to the sgRNA-only and null dSaCas9/sgRNA controls respectively).

Figure 3:
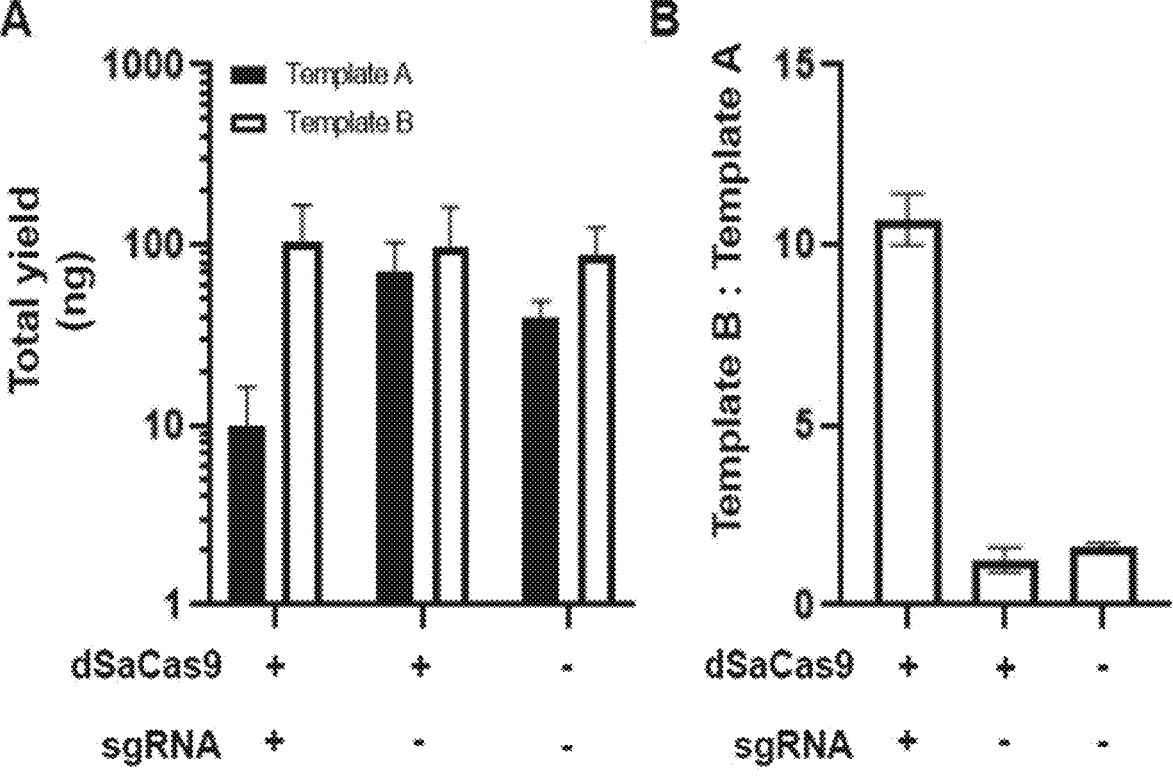
FIG. 3 shows the results of an experiment showing that dSaCas9 is capable of blocking non-target DNA amplification.

As shown in FIG. 3B, phi29 appears to have a slight preference for amplifying Template B over Template A in the absence of dSaCas9::sgRNA blocking (1.3 and 1.6 fold more Template B detected then Template A at the end of the phi29 reaction in the sgRNA-only and null dSaCas9/sgRNA controls respectively). In the presence of the dSaCas9::sgRNA complex however, this ratio increases such that 10.7 fold more Template B was detected than Template A; a clear enrichment effect. dSaCas9 is capable of enriching target DNA by blocking off-target DNA templates. FIG. 3 shows that dSaCas9 is capable of blocking selectively an amplification reaction of one template versus another template. (A-B) sgRNA was produced targeting Template A. Reactions containing ~0.01 ng Template A and B were exposed to either a complex of dSaCas9::sgRNA, dSaCas9 alone, or null dSaCas9/sgRNA as described in the methods section. DNA was amplified using the phi29 enzyme. Outputs of the phi29 reaction were quantified by qPCR. A) shows the total ng output of the reaction, while B) shows the ratio of Template A:B following phi29 amplification. The results show clear blocking of template A amplification when in the presence of sgRNA (A), allowing for greater enrichment of template B in the reaction mix (B). Collectively, these results demonstrate a capacity for the targeted enrichment of target DNA from a mixed DNA population by the dSaCas9::sgRNA complex.

Demonstration of Salt Cycling

Materials and Methods

Enzymes and DNA templates (0.01 ng), along with primers and other reagents were as described above. The "salt cycling" reaction mixture was initially prepared containing dSaCas9, Ph29, primers and templates in a single reaction container having an NaCl concentration of 25 mM. This mixture was incubated for 1 hour at 30° C. NaCl was then added to the reaction mixture to bring the NaCl concentration to 100 mM. The mixture was incubated for 15 minutes at 37° C., before restoring (by dilution) the salt concentration to 25 mM and incubating for 3 hours at 30° C. The "no salt cycling" reaction conditions was a 4 hour and 15 minute incubation at 30° C. at a salt concentration of 25 mM. Further controls were carried out without dSaCas9 and/or without the sgRNA of the dSaCas9 complex.

Copy number of template A and template B were measured as described above by qPCR.

The experiment was repeated to allow error bars to be calculated.

Results and Discussion

Figure 4:
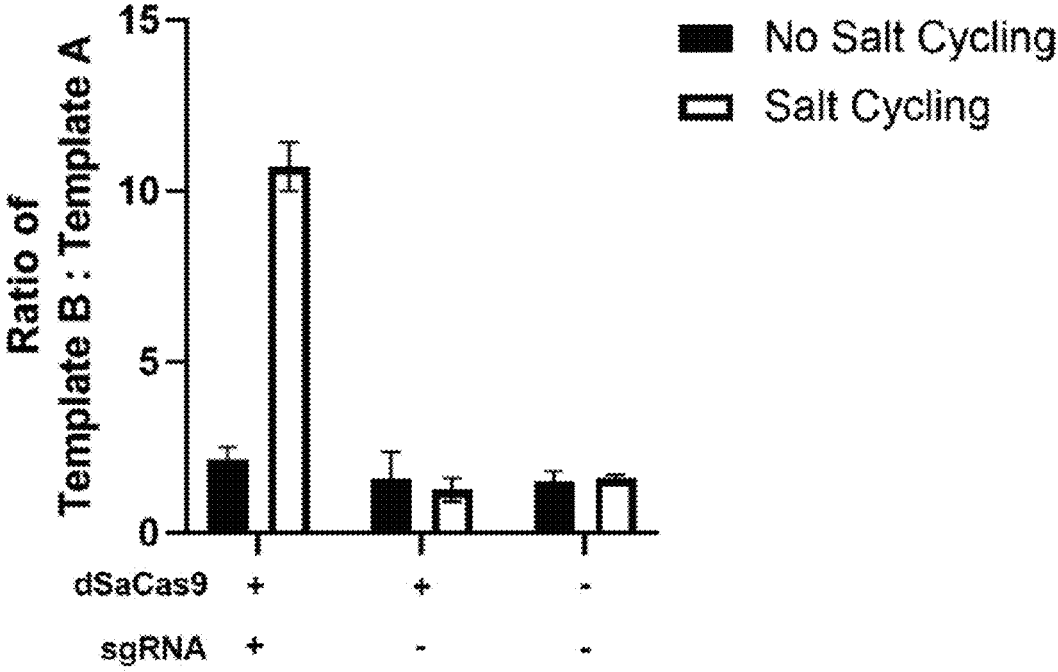
FIG. 4 shows the results of an experiment demonstrating the value of "salt cycling"

The results of this experiment are presented in FIG. 4 which shows the ratio of template B:template A (by copy number as determined by qPCR). If templates A and B have similar amplification efficiencies in the absence of differential amplification one would expect a value of approximately 1 in the graph of FIG. 4. The first column of FIG. 4 shows that with dSaCas9 in the reaction mixture results there is a slight enrichment (about 2-fold) of template B. This can be attributed to a slightly higher amplification efficiency (or possibly a slightly higher detection efficiency) of template B versus template A. It cannot be attributed to the presence of dSaCas9 because it is also seen in columns 5 of FIG. 4 which contains no dSaCas9, and in column 3 of FIG. 4 which contains no template A-specific sgRNA. The inability of dSaCas9 to inhibit amplification of non-target template A under reaction conditions suitable for phi29 polymerisation (25 mM NaCl, 30° C.) is as expected. The results shown in column 2 of FIG. 4 are unexpected, because they show that dSaCas9 is able to inhibit template A under reaction conditions suitable for phi29 polymerisation (25 mM NaCl, ° C.), if the dSaCas9 has previously been incubated with the template under conditions suitable for dSaCas9 binding (100 mM NaCl, 37° C.). The use of the "salt cycling" protocol results in an approximately 5-fold improvement in the ratio of template B to template A. That effect is dependent in dSaCaas9 and is sequence specific and mediated via the dSaCas9 sgRNA is confirmed, respectively, by columns 6 and 4 of FIG. 4 which show that the effect is abolished in the absence of dSaCas9 and in the presence of dSacas9 without sgRNA.

---

The invention claimed is:

1. A method of selective DNA multiple displacement amplification (MDA) of a DNA mixture comprising a first population of DNA and a second population of DNA, comprising:

a) providing a catalytically dead *Staphylococcus aureus* Cas9 complex (dSaCas9) comprising a dSaCas9 protein or derivative thereof complexed with one or more guide RNAs having selective binding affinity for DNA sequences more present in the first population of DNA compared to the second population of DNA and contacting said Cas9 complex with the DNA mixture under a first reaction condition, said first reaction condition being suitable for binding of the dSaCas9 complex to DNA sequences for which it has a binding affinity, and then b) contacting a strand-displacing DNA polymerase with the DNA mixture under a second reaction condition, said second reaction condition being suitable for amplification activity of the strand-displacing DNA polymerase;

wherein the first reaction condition has a higher free salt concentration than the second reaction condition, wherein the first reaction condition has a free salt concentration of above 50 mM NaCl, and wherein the second reaction condition has a free salt concentration of below 50 mM NaCl.

2. The method of claim 1, further comprising:

a) contacting a strand-displacing DNA polymerase with the DNA mixture under a second reaction condition, said second reaction condition being suitable for amplification activity of the strand-displacing DNA polymerase, then b) contacting a catalytically dead *Staphylococcus aureus* Cas9 complex (dSaCas9) comprising a dSaCas9 protein or derivative thereof complexed with one or more guide RNAs having selective binding affinity for DNA sequences more present in the first population of DNA compared to the second population of DNA with the DNA mixture under a first reaction condition, said first reaction condition being suitable for binding of the dSaCas9 complex to DNA sequences for which it has a binding affinity, and then c) contacting a strand-displacing DNA polymerase with the DNA mixture under a second reaction condition, said second reaction condition being suitable for amplification activity of the strand-displacing DNA polymerase, and then, d) optionally repeating steps b) and c) in that order one or more times, wherein the first reaction condition has a higher free salt concentration than the second reaction condition.

3. The method according to claim 1 wherein step a) is carried out in the presence of the strand-displacing DNA polymerase of step b) and wherein step b) is carried out in the presence of the dSaCas9 of step a).

4. The method according to claim 1, wherein the first population of DNA is human genomic DNA and the second population of DNA is bacterial DNA.

5. The method according to claim 1, wherein the strand displacing DNA polymerase is φ29 DNAP or a derivative thereof.

6. The method of claim 1, wherein the first reaction condition has a free salt concentration of between 10 mM and 100 mM NaCl.

7. The method according to claim 1, wherein the second reaction condition has a free salt concentration of between 10 mM and 50 mM NaCl.

8. The method according to claim 1, wherein the first reaction condition has a temperature of between 30° C. and 45° C.

9. The method according to claim 1, wherein the second reaction condition has a temperature of between 20° C. and 35° C.

10. The method according to claim 1, wherein the second reaction condition has a temperature of between 40° C. and 50° C.

11. The method according to claim 4, which is preceded by the step of preparing a sample previously obtained from a human subject to obtain the DNA mixture, wherein said human subject has sepsis or is suspected of having sepsis.

12. The method according to claim 11, further comprising an additional step, prior to preparing a sample previously obtained from a human subject, of obtaining the sample from the human subject.

13. The method according to claim 12, further comprising a subsequent step of carrying out whole genome sequencing on one or more bacterial species in the amplified DNA to produce one or more bacterial whole genome sequences.

14. The method according to claim 11, further comprising a step of analysing one or more of the one or more bacterial whole genome sequences to select an antibiotic or combination of antibiotics effective to kill or inhibit growth of the one or more bacterial species, and optionally administering said antibiotic or combination of antibiotics to the human subject.

15. The method according to claim 1, wherein the method comprises changing from a reaction condition having a relatively high free salt concentration to a reaction condition having a relatively low free salt concentration by the addition of a salt dilution agent.

16. The method according to claim 1, wherein the method comprises changing from a reaction condition having a relatively low free salt concentration to a reaction condition having a relatively high free salt concentration by the addition of a salt sequestering, chelating or precipitating agent.

17. The method according to claim 1, wherein the method comprises changing from a reaction condition having a relatively high free salt concentration to a reaction condition having a relatively low free salt concentration by removal of salt or the addition of water across a dialysis membrane.

18. The method according to claim 1, wherein the method comprises changing from a reaction condition having a relatively low free salt concentration to a reaction condition having a relatively high free salt concentration by removal of water or the addition of salt across a dialysis membrane.

\* \* \* \* \*

SEQUENCE LISTING

```
Sequence total quantity: 6
SEQ ID NO: 1            moltype = AA  length = 1222
FEATURE                 Location/Qualifiers
source                  1..1222
                        mol_type = protein
                        organism = Synthetic construct
SEQUENCE: 1
MSDKIIHLTD DSFDTDVLKA DGAILVDFWA EWCGPCKMIA PILDEIADEY QGKLTVAKLN 60
IDQNPGTAPK YGIRGIPTLL LFKNGEVAAT KVGALSKGQL KEFLDANLAG SGSGHMHHHH 120
HHSSGLVPRG SGMKETAAAK FERQHMDSPD LGTDDDDKMP KKKRKVEASM KRNYILGLAI 180
GITSVGYGII DYETRDVIDA GVRLFKEANV ENNEGRRSKR GARRLKRRRR HRIQRVKKLL 240
FDYNLLTDHS ELSGINPYEA RVKGLSQKLS EEEFSAALLH LAKRRGVHNV NEVEEDTGNE 300
LSTKEQISRN SKALEEKYVA ELQLERLKKD GEVRGSINRF KTSDYVKEAK QLLKVQKAYH 360
QLDQSFIDTY IDLLETRRTY YEGPGEGSPF GWKDIKEWYE MLMGHCTYFP EELRSVKYAY 420
NADLYNALND LNNLVITRDE NEKLEYYEKF QIIENVFKQK KKPTLKQIAK EILVNEEDIK 480
GYRVTSTGKP EFTNLKVYHD IKDITARKEI IENAELLDQI AKILTIYQSS EDIQEELTNL 540
NSELTQEEIE QISNLKGYTG THNLSLKAIN LILDELWHTN DNQIAIFNRL KLVPKKVDLS 600
QQKEIPTTLV DDFILSPVVK RSFIQSIKVI NAIIKKYGLP NDIIIELARE KNSKDAQKMI 660
NEMQKRNRQT NERIEEIIRT TGKENAKYLI EKIKLHDMQE GKCLYSLEAI PLEDLLNNPF 720
NYEVDHIIPR SVSFDNSFNN KVLVKQEEAS KKGNRTPFQY LSSSDSKISY ETFKKHILNL 780
AKGKGRISKT KKEYLLEERD INRFSVQKDF INRNLVDTRY ATRGLMNLLR SYFRVNNLDV 840
KVKSINGGFT SFLRRKWKFK KERNKGYKHH AEDALIIANA DFIFKEWKKL DKAKKVMENQ 900
MFEEKQAESM PEIETEQEYK EIFITPHQIK HIKDFKDYKY SHRVDKKPNR ELINDTLYST 960
RKDDKGNTLI VNNLNGLYDK DNDKLKKLIN KSPEKLLMYH HDPQTYQKLK LIMEQYGDEK 1020
NPLYKYYEET GNYLTKYSKK DNGPVIKKIK YYGNKLNAHL DITDDYPNSR NKVVKLSLKP 1080
YRFDVYLDNG VYKFVTVKNL DVIKKENYYE VNSKCYEEAK KLKKISNQAE FIASFYNNDL 1140
IKINGELYRV IGVNNDLLNR IEVNMIDITY REYLENMNDK RPPRIIKTIA SKTQSIKKYS 1200
TDILGNLYEV KSKKHPQIIK KG 1222

SEQ ID NO: 2            moltype = RNA  length = 21
FEATURE                 Location/Qualifiers
source                  1..21
                        mol_type = other RNA
                        organism = synthetic construct
SEQUENCE: 2
gcgcggcggt gattttgtgc c                                       21

SEQ ID NO: 3            moltype = RNA  length = 21
FEATURE                 Location/Qualifiers
source                  1..21
                        mol_type = other RNA
                        organism = Synthetic construct
SEQUENCE: 3
attgggagca gtttcgctgg t                                       21

SEQ ID NO: 4            moltype = RNA  length = 22
FEATURE                 Location/Qualifiers
source                  1..22
                        mol_type = other RNA
                        organism = synthetic construct
SEQUENCE: 4
gtccgtcgtc gaagccactt ct                                      22

SEQ ID NO: 5            moltype = RNA  length = 79
FEATURE                 Location/Qualifiers
source                  1..79
                        mol_type = other RNA
                        organism = synthetic construct
SEQUENCE: 5
gttttagtac tctggaaaca gaatctacta aaacaaggca aaatgccgtg tttatctcgt 60
```

-continued

```
caacttgttg gcgagattt                                                79

SEQ ID NO: 6          moltype = AA  length = 575
FEATURE               Location/Qualifiers
source                1..575
                      mol_type = protein
                      organism = synthetic construct
SEQUENCE: 6
MKHMPRKMYS CDFETTTKVE DCRVWAYGYM NIEDHSEYKI GNSLDEFMAW VLKVQADLYF   60
HNLKFDGAFI INWLERNGFK WSADGLPNTY NTIISRMGQW YMIDICLGYK GKRKIHTVIY  120
DSLKKLPFPV KKIAKDFKLT VLKGDIDYHK ERPVGYKITP EEYAYIKNDI QIIAEALLIQ  180
FKQGLDRMTA GSDSLKGFKD IITTKKFKKV FPTLSLGLDK EVRYAYRGGF TWLNDRFKEK  240
EIGEGMVFDV NSLYPAQMYS RLLPYGEPIV FEGKYVWDED YPLHIQHIRC EFELKEGYIP  300
TIQIKRSRFY KGNEYLKSSG GEIADLWLSN VDLELMKEHY DLYNVEYISG LKFKATTGLF  360
KDFIDKWTYI KTTSEGAIKQ LAKLMLNSLY GKFASNPDVT GKVPYLKENG ALGFRLGEEE  420
TKDPVYTPMG VFITAWARYT TITAAQACYD RIIYCDTDSI HLTGTEIPDV IKDIVDPKKL  480
GYWAHESTFK RAKYLRQKTY IQDIYMKEVD GKLVEGSPDD YTDIKFSVKC AGMTDKIKKE  540
VTFENFKVGF SRKMKPKPVQ VPGGVVLVDD TFTIK                             575
```